United States Patent
Popescu et al.

(10) Patent No.: US 7,421,058 B2
(45) Date of Patent: Sep. 2, 2008

(54) DEVICE FOR NON-CONTACTING TRANSMISSION OF ELECTRICAL SIGNALS BETWEEN TWO RELATIVELY MOVING PARTS, WITH REDUCED PERTURBING RADIATION

(75) Inventors: Stefan Popescu, Erlangen (DE); Marco Leone, Olching (DE)

(73) Assignee: Siemens Aktiengesellschaft, Munich (DE)

( * ) Notice: Subject to any disclaimer, the term of this patent is extended or adjusted under 35 U.S.C. 154(b) by 33 days.

(21) Appl. No.: 11/494,869

(22) Filed: Jul. 28, 2006

(65) Prior Publication Data

US 2007/0040635 A1 Feb. 22, 2007

Related U.S. Application Data

(60) Provisional application No. 60/704,087, filed on Jul. 29, 2005.

(30) Foreign Application Priority Data

Nov. 24, 2005 (DE) .................. 10 2005 056 049

(51) Int. Cl.
*H05G 1/08* (2006.01)
(52) U.S. Cl. ...................... 378/20; 333/24 R
(58) Field of Classification Search .......... 378/20, 378/15, 197, 101; 439/11–30; 385/26; 333/261, 333/24 R
See application file for complete search history.

(56) References Cited

U.S. PATENT DOCUMENTS

| | | | |
|---|---|---|---|
| 5,210,523 A | 5/1993 | Tipping | |
| 5,530,422 A * | 6/1996 | Harrison | 340/500 |
| 5,530,425 A | 6/1996 | Harrison | |
| 5,646,962 A * | 7/1997 | Harrison | 375/308 |
| 5,734,658 A | 3/1998 | Rall et al. | |
| 6,301,324 B1 | 10/2001 | Pearson, Jr. et al. | |
| 6,956,450 B1 | 10/2005 | Lohr | |
| 2003/0003776 A1 | 1/2003 | Lohr et al. | |

FOREIGN PATENT DOCUMENTS

DE 1 298 168 7/1967
EP 1 051 816 5/2002

OTHER PUBLICATIONS

Designing Controlled-Impedance Vias, Neu, Electronic Design News, Oct. 2, 2003, pp. 67-72.

* cited by examiner

*Primary Examiner*—Hoon Song
(74) *Attorney, Agent, or Firm*—Schiff Hardin LLP

(57) ABSTRACT

A device for non-contacting transmission of electrical signals between one part moving relative to another part has at least one strip conductor pair for symmetrical signal transmission attached on a first of the two parts, in which strip conductor pair the electrical signals are supplied from a transmission module for differential signal transmission. At least one reception element is attached on the other of the two parts, at a slight separation along at least one segment of the strip conductor pair, and is connected with a reception module. The strip conductor pair is provided with one or more components for reduction of a common mode signal component that arises therein due to the differential signals therein. Additionally or alternatively, compensation elements for adaptation of a time offset between signals on the output conductors are arranged in the output conductors of the transmission module that minimizes the common mode signal component. A reduced electromagnetic perturbing radiation is achieved with the device during the non-contacting signal transmission by capacitive RF coupling.

19 Claims, 5 Drawing Sheets

FIG 8
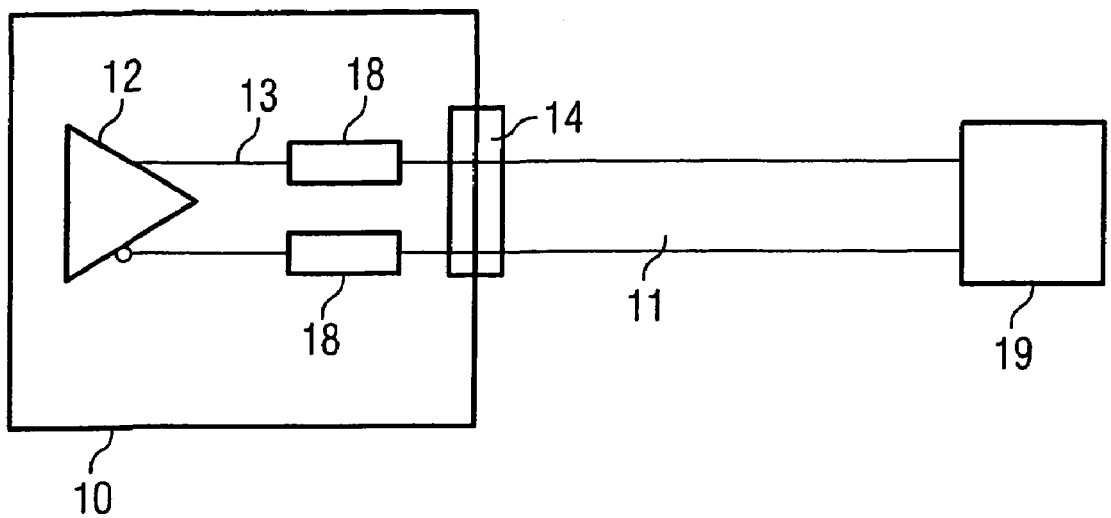
FIG 9A
FIG 9B
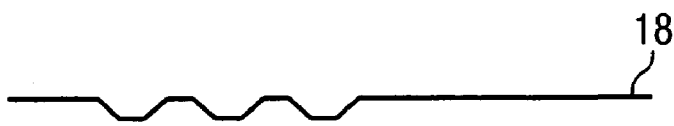
FIG 9C
FIG 9D
FIG 10
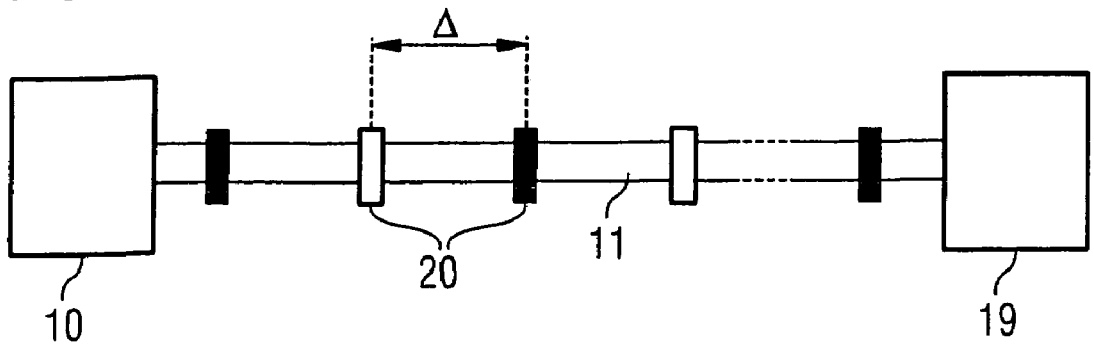

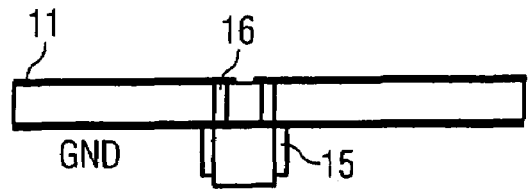
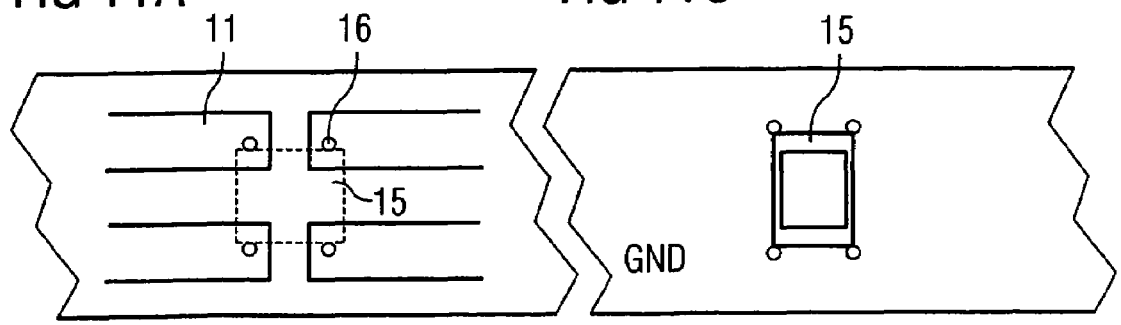
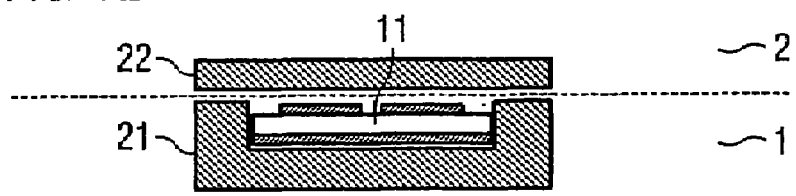
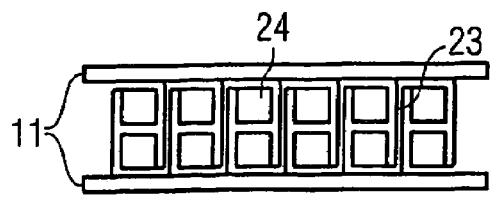
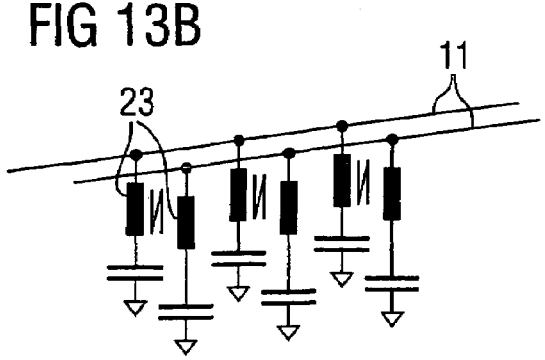

DEVICE FOR NON-CONTACTING TRANSMISSION OF ELECTRICAL SIGNALS BETWEEN TWO RELATIVELY MOVING PARTS, WITH REDUCED PERTURBING RADIATION

CROSS-REFERENCE TO RELATED APPLICATION

The present application claims the benefit of U.S. Provisional Application No. 60/704,087, filed Jul. 29, 2005, which is hereby incorporated herein by reference.

BACKGROUND OF THE INVENTION

1. Field of the Invention

The present invention concerns a device for non-contacting transmission of electrical signals between a part moving relative to another part, of the type wherein at least one strip conductor pair for symmetrical signal transmission is applied on a first of the two parts (in which strip conductor pair the electrical signals are fed from a transmission module for differential signal transmission) and in which at least one reception element is attached on a second of the two parts, the reception element moving during the relative movement of the two parts at a slight separation along at least one segment of the strip conductor pair, and being connected with a reception module. Such a device is suitable for the non-contacting transfer of data between the rotating part and the stationary part of a computed tomography apparatus.

2. Description of the Prior Art

In the operation of a computed tomography apparatus, the data acquired by the x-ray detectors must be transferred from the rotating part to the stationary part of the system in order to be further processed. The data quantity to be transferred per time unit constantly increases with the further development of computed tomography systems, particularly computed tomography systems of the third generation. The devices that are available for data transfer (such as the known slip rings operating without contact) are limited in terms of the transfer rate. A need therefore exists to use a number of these slip rings in parallel (next to one another) in order to achieve an increased transfer rate by a simultaneous data transfer in real time.

In the non-contacting transmission of electrical signals using slip rings, use is made of the electrical field that arises given the feed of electrical signals at the slip ring. Through (normally capacitive) coupling, these signals can be coupled into a reception element past which the slip ring moves at a slight distance. This reception element is arranged at the stationary part of the computed tomography apparatus and is connected with a reception module for decoding the received signals. The slip ring is normally fashioned as a strip conductor in which the electrical field modulated with the fed electrical signals can propagate. Such a strip conductor, however, also leads to unwanted electromagnetic radiation that is called electromagnetic perturbing radiation. This perturbing radiation accumulates given the usage of a number of strip conductors, as can be necessary for a high data transfer rate. This can lead to the situation that the required electromagnetic compatibility (EMC) for medical apparatuses can no longer be maintained. The perturbing radiation already varies very significantly due to manufacturing tolerances from component to component and additionally depends on the spectral composition of the transmitted signals.

To reduce the electromagnetic perturbing radiation given non-contacting data transfer in computed tomography systems, it is known (for example from EP 1 051 816 B1) to significantly spectrally spread the signals to be transmitted in order to reduce the radiated perturbation level by decreasing the average spectral power density. For serial high-speed data transfer, however, this technique cannot be used since the requirements for the lack of jitter of the components used are too high with higher data rates.

Shielding of the strip conductor is proposed in U.S. Pat. No. 5,530,425, but does not operate efficiently enough at high data rates in order to justify the complexity and the resulting costs required for such shielding.

A further known technique for reduction of electromagnetic perturbing radiation is the use of a strip conductor pair through which the electrical signals are differentially transmitted. The coupling that occurs between two strip conductors lying close to one another is utilized. Such a strip conductor pair enables the propagation of directed electromagnetic waves in a push-pull mode (differential mode) or in common mode (push-push mode). In differential signal transmission, the signals to be transmitted are coupled into both strip conductors of the strip conductor pair offset by 180° in terms of phase. This leads to a difference voltage between the two strip conductors that correspond to twice the signal amplitude. In the common mode signal transmission, the signal is coupled into both strip conductors with the same phase such that no voltage difference exists between the two strip conductors.

Differential signal transmission has the advantage that, in the ideal case, the electromagnetic waves radiated by the two strip conductors of the strip conductor pair mutually compensate in the far field, and thus no perturbing radiation, or only very slight perturbing radiation, occurs. Differential signal transmission via strip conductor pair is therefore utilized in U.S. Pat. No. 5,530,422 in order to achieve a non-contacting signal transmission between the rotating part and the stationary part of a computed tomography apparatus with reduced perturbing radiation. The differential impedance of a symmetrical strip conductor pair corresponds to twice the impedance of the individual strip conductor minus the impedance that results due to the electromagnetic coupling of the two strip conductors. A strong coupling due to a close arrangement of both strip conductors reduces the differential impedance, but increases the common mode impedance. Under the opposite conditioning, the differential impedance approaches the sum of both individual impedances of the strip conductors when only a very weak coupling of both strip conductors exists. In U.S. Pat. No. 5,530,422 (already cited), a parallel termination is employed for both strip conductors. This termination can be a good termination for differential signal transmission, but not for common mode signals.

A problem in the usage of the technique of differential signal transmission is that no ideal compensation of the radiated electromagnetic fields is achieved in the far field due to tolerances of the components of the transmission module, or due to different conductor lengths, or material inhomogeneities of both strip conductors of the strip conductor pair. Rather, due to such tolerances the electromagnetic perturbing radiation can assume high values, which are always undesirable.

SUMMARY OF THE INVENTION

An object of the present invention is to provide a device for non-contacting transmission of electrical signals between one part moving relative to another part, with which reduced electromagnetic perturbing radiation is achieved.

The object is achieved in accordance with the invention by a device for non-contacting transmission of electrical signals between one part moving relative to another part, wherein at least one strip conductor pair for symmetrical signal transmission is attached on a first of the two parts, in which strip conductor pair the electrical signals are supplied from a transmission module for differential signal transmission. At least one reception element is attached on the second of the two parts, at a slight separation along at least one segment of the strip conductor pair and is in communication with a reception module. The strip conductor pair and the reception element are in coupled relationship during the relative movement so that signals corresponding to the differential signals are detected by the reception element. The strip conductor pair is provided with one or more components for reduction of a parasitic common mode signal component and/or compensation elements for adaptation of a time offset between signals on the output conductors (lines) are arranged in the output conductors of the transmission module.

The inventive device is based on the recognition that, in differential signal transmission, a parasitic common mode signal component is a significant cause for the electromagnetic perturbing radiation in the far field. Even very small unwanted asymmetries in the differential signal transmission lead to standing common mode waves in the strip conductor pair that cause electromagnetic perturbing radiation. To reduce this electromagnetic perturbing radiation, the strip conductor pair is therefore provided with one or more components to reduce the parasitic common mode signal component and/or in the transmission module, the compensation elements cause the common mode signal component supplied into the strip conductor pair by the transmission module to be minimized. By one or both of these measures, the electromagnetic perturbing radiation is substantially reduced during differential signal transmission.

In an embodiment of the device, the one or more components to reduce the parasitic common mode signal component are termination resistors with which the strip conductor pair is terminated both for the common mode signal component and for the push-pull signals. This embodiment is based on the recognition that a non-optimal termination with regard to common mode signals leads to resonant standing waves in the strip conductor pair that cause the perturbing radiation. Although a parallel termination for a good termination of the differential signal portions is used in the differential signal transmission according to the prior art, as explained in connection with U.S. Pat. No. 5,530,422, the present embodiment additionally provides for an optimal termination of possible parasitic common mode signal components. In the present invention, the termination of the strip conductor pair ensues with a termination resistor network composed of at least three resistors in a T-connection; but it can also be realized by other network structures, for example a Π-structure.

In a version of this embodiment, the termination resistors are attached on the underside of a printed circuit board and connected with the strip conductors on the top side of the circuit board by feedthroughs (known as "vias") adapted (matched) in terms of impedance. Such vias with adapted impedance reduce reflections at this point that can lead to an increased electromagnetic perturbing radiation. An example for the design of such vias adapted in terms of impedance is described in the publication by T. Neu, "Designing Controlled-Impedance Vias", Electronic Design News, Oct. 2, 2003, pages 67-72. Such vias adapted in terms of impedance preferably are used in all feedthroughs of the present device that are connected with the strip conductors, as well as in the subsequent embodiments.

In a further embodiment or development of the present device, the strip conductor pair is divided into a number of separate segments that are connected with one another by common mode chokes. The common mode chokes damp (attenuate) common mode signal components so that these cannot accumulate over the entire length of the strip conductor pair.

A minimization of the common mode signal component in the strip conductor pair also can be achieved by other components. In a further embodiment, the strip conductor pair is at least partially enclosed by one or more elements made of a ferrite material. These elements can extend over the entire length of the strip conductor pair, or can be distributed along the strip conductor pair. For this purpose one or more U-shaped elements are used, having a U-shaped channel in which the strip conductor pair is arranged. These elements made of ferrite material act as common mode signal chokes, because they likewise prevent the formation of a larger common mode signal component during differential signal transmission. A strip made of ferrite material can e attached on the (second) part that is provided with the reception element, this ferrite strip being located over the strip conductor pair or the opening of the U-shaped elements during the relative movement of both parts.

In a further embodiment of the device in which the formation of a larger common mode signal component is likewise prevented, structures on the printed circuit board are fashioned as stubs that are capacitively terminated and strongly coupled with the strip conductor pair. These strongly coupled stubs likewise behave as common mode chokes. The capacitive termination can be achieved by relatively large (for example rectangular) metallic surfaces on the circuit board.

In a further embodiment of the device, the one or more components include at least one common mode choke to reduce the common mode signal component, the common mode choke being arranged on an input-side end of the strip conductor pair. This common mode choke is thus located in direct connection with the strip conductor pair between the strip conductor pair and the connector with the transmission module. Common mode signals that result from the connection of the strip conductors with the transmission module can be reduced in this manner. A common mode choke is preferably used that exhibits a relatively low impedance and thus operates less effectively than a common mode signal choke with high impedance. Common mode signal chokes with high impedance do in fact suppress common mode signal components more strongly, but they distort the signal quality of high-speed signals. The impedance of the common mode choke therefore is selected such that the electromagnetic compatibility requirements of the device with regard to the signal transmission can be directly achieved in combination with other measures embodied in the device.

In addition, or as an alternative, to the components for reduction of the common mode signal component at the strip conductor pair, the inventive device can have a transmission module with compensation elements that minimize an unwanted time offset between the two output conductors of the transmission module. In the ideal case, the electrical signals provided on both output conductors for the differential signal transmission would be phase-shifted by exactly 180°. Due to tolerances and component scatter, however, an unwanted time offset frequently arises between the two output conductors. Compensation elements therefore can be provided in both output conductors in the device, the compensation elements already compensating the unwanted time offset in the production of the transmission module. These can be suitable delay segments in the output conductors that can be adapted (tuned) in production of the device with regard to the delay generated by them.

The aforementioned embodiments can be divided into three different categories. In a first category, an unwanted common mode signal component is minimized already in the transmission module or directly before the feed of the signal into the strip conductor pair. This ensues directly at the input-side end of the strip conductor pair by the compensation elements in the transmission module as well as the common mode signal choke(s). In a second category, the creation of standing common mode waves in the strip conductor pair is suppressed by a termination of the pain that is effective with regard to the differential signals and with regard to the common mode signal component. In a third category, the common mode signal component on the strip conductor pair is damped (which common mode signal component can form due to inhomogeneities along the conductors by damping elements for this common mode signal component arranged in or on the strip conductor pair. The individual measures can be implemented alone or in arbitrary combination in the present device.

The device is primarily suited for the non-contacting capacitive RF signal transmission between the rotating part and the stationary part of a computed tomography apparatus, but the device can used as well in all other application fields in which a signal transmission occurs between two parts moving relative to one another that are located closely adjacent during the relative movement. Other examples are industrial scanners and baggage scanners that are used for security control in airports.

DESCRIPTION OF THE DRAWINGS

FIG. 8 shows an example for the embodiment of the transmission module with compensation elements in accordance with the invention.

FIGS. 9A-9D show examples for the embodiment of a compensation element in accordance with the invention.

FIG. 10 shows an example for the arrangement of a number of common mode chokes in strip conductor pairs in accordance with the invention.

FIGS. 11A-11C shows examples for the connection of the common mode chokes with the strip conductor pair in accordance with the invention.

FIG. 12 shows an example for the use of elements made of a ferrite material in accordance with the invention.

FIGS. 13A-13B show examples for the use of common mode chokes in the form of suitable structures on the circuit board in accordance with the invention.

DESCRIPTION OF THE PREFERRED EMBODIMENTS

Figure 1:
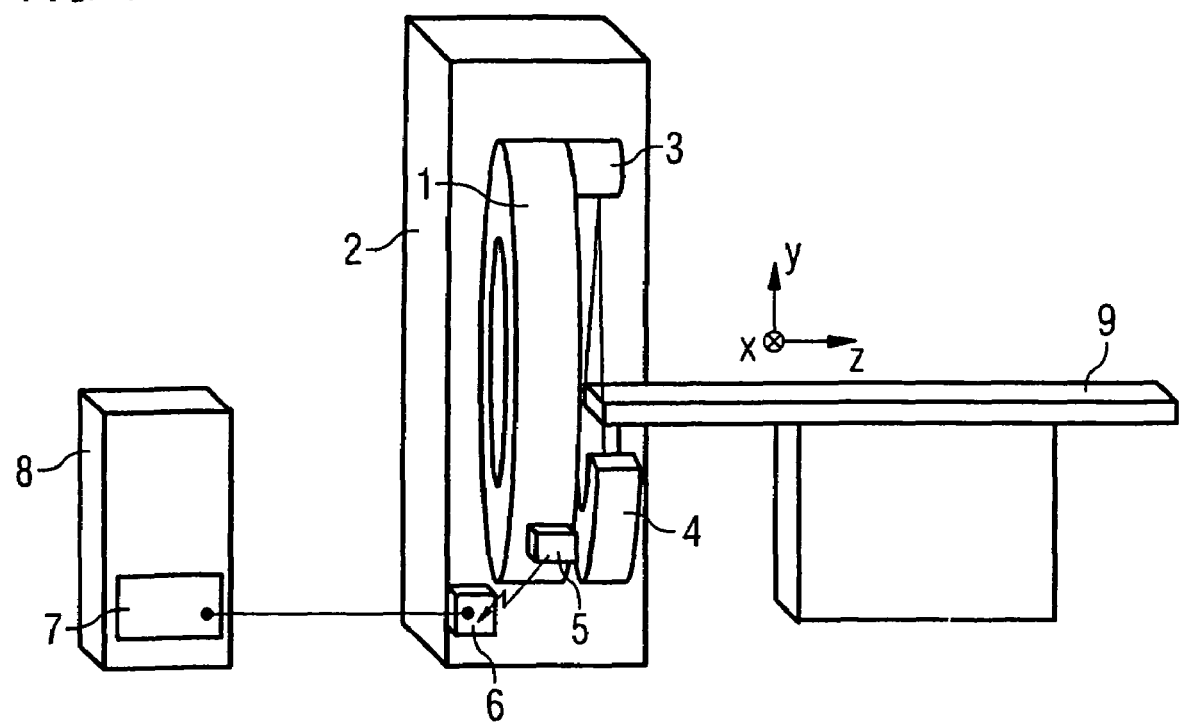
FIG. 1 schematically shows the basic design of a computed tomography apparatus in which the inventive device can be used.

In schematized representation, FIG. 1 shows a computed tomography apparatus with a signal transmission device for transmission of measurement data from the rotating part 1 to the stationary part 2 of the gantry. Among other things, the computed tomography apparatus has an x-ray tube 3, x-ray detectors 4 arranged linearly, and a patient positioning table 9. The x-ray tube 3 and the x-ray detectors 4 are arranged at the rotating part 1 of the gantry, which rotates around the patient positioning table 9 or an examination axis Z running parallel thereto. The patient positioning table 9 normally can be displaced relative to the gantry along the examination axis Z. The x-ray tube 3 emits an x-ray beam spreading in a fan shape in a slice plane perpendicular to the examination axis Z. The x-ray beam penetrates a slice of a subject (for example a body slice of a patient who is positioned on the patient positioning table 9 in examinations) and strikes the x-ray detectors 4 situated opposite the x-ray tube 3. The angle at which the x-ray beam penetrates the body slice of the patient and, if applicable, the position of the patient positioning table 9 relative to the gantry vary continuously during the image acquisition with the computed tomography apparatus. During the image acquisition, the x-ray detectors 4 deliver a large quantity of measurement data that must be evaluated for reconstruction of a two-dimensional slice image or a three-dimensional image of the body of the patient. The evaluation normally ensues in a stationary computer system 8 that is connected with the computed tomography apparatus.

During the data acquisition, the rotating part 1 of the gantry rotates within the stationary part 2. The measurement data acquired by the x-ray detectors 4 are transferred to a stationary reception device 6 at the stationary part 2 of the computed tomography apparatus with a rotating transmission device 5 that is attached to the rotating part 1 of the gantry. The data are then normally supplied via a cable connection from the stationary reception device 6 to a receiver 7 of the image computer 8 for evaluation. The transmission device 5 and the reception device 6 are shown only schematically in FIG. 1. The transmission device 5 includes one or more pairs of strip conductors (in particular micro-strip conductors) on the rotating part 1 that extend around the entire rotating part 1. The reception device 6 includes at least one element acting as a reception antenna (for example a short piece of a strip conductor) that is located in immediate proximity over the strip conductor pair of the transmission device 5 during the rotating movement of the gantry. The basic design of such a signal transmission device (also known as a slip ring) is known from the prior art.

Figure 2:
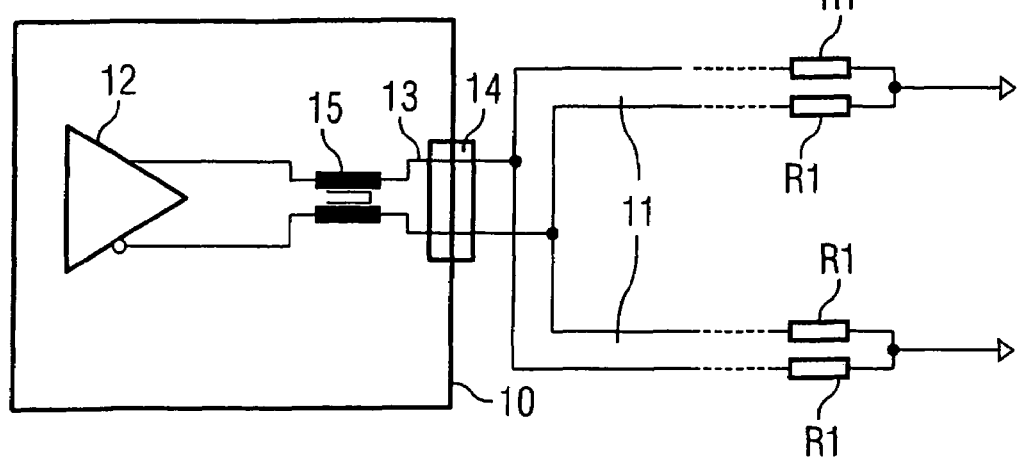
FIG. 2 is an example for the termination of a differential strip conductor pair according to the prior art.

FIG. 2 shows an example for the electrical design of the transmitter-side part of such a transmission device according to the prior art. The strip conductor pair 11 is connected in parallel at both ends via two respective resistors $R_1$. The signals to be transmitted are fed from the transmitter module 10 into the strip conductor pair 11. For this purpose, the supplied signals are provided to both output conductors 13 of the transmission module 10 phase-shifted by 180° by a differential driver. A common mode choke 15 (normally a current-compensating transformer) is connected between the connector 14 with the strip conductor pair 11 and the differential driver 12 to minimize the common mode signal component (which is almost always present). This common mode choke 14 attenuates the common mode signal component that results from component tolerances and asymmetries within the transmission module 10. Since the transmission module 10 is connected with the strip conductor pair 11 via the connector 14, additional asymmetries can result from the design and from resistance spikes in the connector 14.

Figure 5:
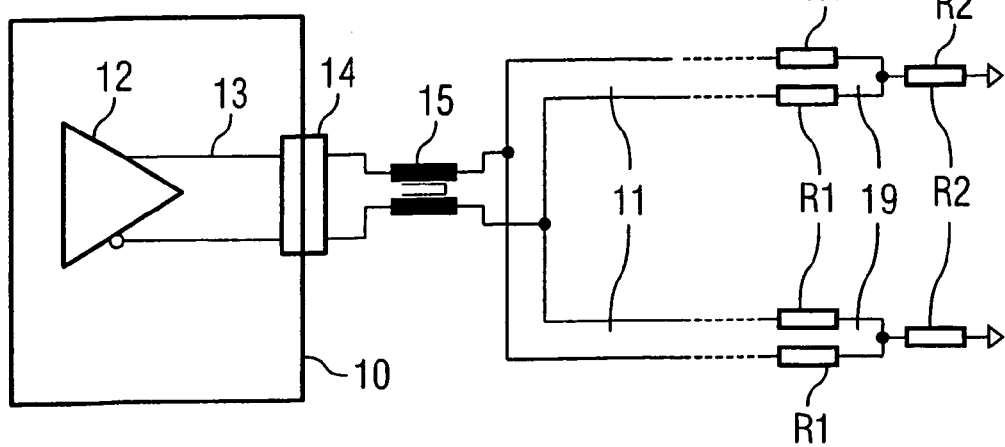
FIG. 5 shows an example for a further embodiment of the inventive device with an input-side common mode choke.

In an embodiment of the present device shown in FIG. 5, a common mode choke 15 is directly connected with the input-side end of the strip conductor pair 11. This common mode choke 15 is thus arranged after the connector 14 such that it also suppresses common mode signal components generated by the connector before these are injected into the strip conductor pair 11.

Figure 6:
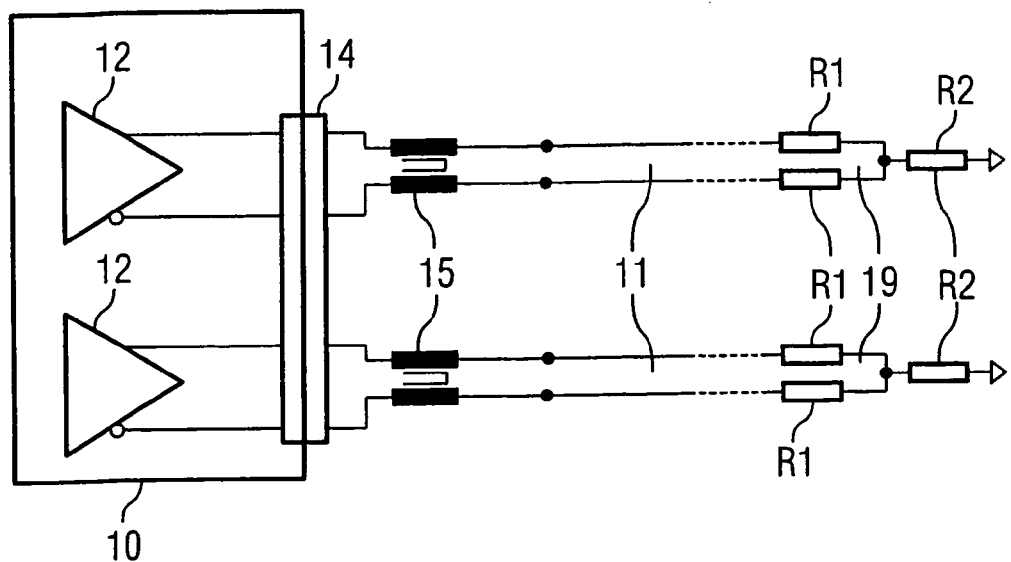
FIG. 6 shows an example for a further embodiment of the inventive device with two strip conductor drivers that are independent of one another.

FIG. 6 shows a further example in which two separate differential strip conductor pairs 11 are used. These strip conductor pairs 11 are connected via separate common mode chokes 15 with separate differential drivers 12 in the transmission module 10, as this is apparent from FIG. 6.

Figure 7A:
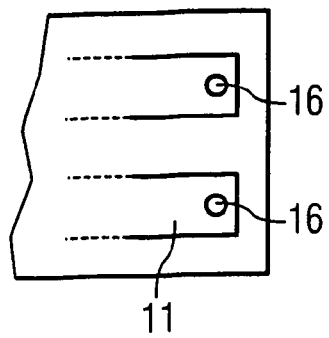
FIGS. 7A-7C show an example for the connection of the input-side common mode choke with the strip conductor pair in accordance with the invention.
Figure 7B:
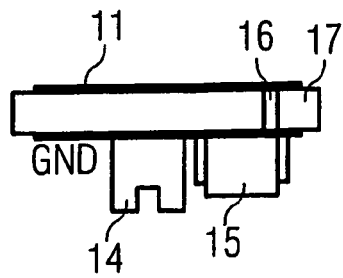
Figure 7C:
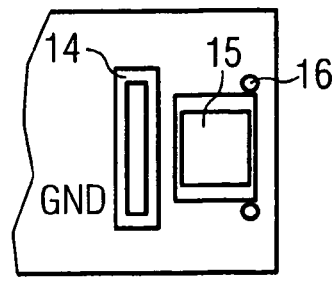

The connection of the common mode chokes 15 with the respective strip conductor pair 11 ensues by feedthroughs (vias) 16 with adapted (matched) impedance through the circuit board 17 on the front side of which the strip conductors 11 are attached. Both the connectors 14 and the common mode chokes 15 are arranged on the back side of the circuit board 17. FIG. 7A shows the top side of the circuit board, FIG. 7B shows a cross-section through the circuit board, and FIG. 7C is a view of the underside. In contrast to the typical usage of simple feedthroughs or groove connections, the feedthroughs 16 with adapted impedance that are used in the present example eliminate reflections that arise due to resistance spikes at these feedthroughs, which lead to higher (stronger) common mode signal components. Common mode chokes of high impedance are in fact more efficient for suppression of common mode waves, however they distort the high-speed signals to be transmitted. This distortion grows with increasing impedance. A common mode choke with an impedance that directly supplies the necessary degree of common mode wave suppression that is necessary for adherence to the EMC compatibility requirements of the particular application therefore must be selected for usage in the present device. This can be achieved by suitable selection of the electrical and mechanical parts of the common mode choke. A common mode choke with low impedance is advantageously used, but further measures then are implemented for reduction of the common mode signal component in the transmitter module 10.

FIGS. 8 and 9A-9D show examples for a further measure. Compensation elements 18 are used for compensation of an unwanted time delay between the two output conductors 13 of the transmission module 10. In the ideal case, the time delay between the two output conductors is 0, such that both signal portions are phase-shifted exactly by 180° on both output conductors 13 for the differential signal transmission. In practice, however, a time offset occurs between the two output conductors 13. This time offset leads to the generation of short common mode pulses that couple common mode waves in the strip conductor pair and thus lead to increased electromagnetic perturbing radiation. Due to production tolerances of the components, inherent asymmetries in the layout of the circuit boards used or in the output connectors, the unwanted asymmetry cannot be completely corrected even with careful selection of the components used. The unwanted time offset leads to a mode conversion in which a portion of the signal power of the differential signal is converted into signal power for the common mode signal. Even if both output conductors exhibit exactly corresponding lengths, the time offset nevertheless can be caused by the differential drivers. In many cases the driver asymmetry is not specified. In these cases, it can be assumed that the temporal offset is at least 10% of the signal rise time (ramp response). For example, a 2.5 Gbit/s driver with a rise time of 200 ps thus exhibits an output offset of at least 20 ps or worse.

In the embodiment of FIG. 8, the compensation elements 18 with which a time offset between the two output conductors can be compensated are therefore introduced into the output conductors 13. These compensation elements represent delay lines with adjustable delay. These are hereby preferably micro-strip conductors that are already suitably set in terms of the delay given the production of the transmitter module 10.

FIGS. 9A-9D show examples for such compensation elements 18 fashioned as micro-strip conductors. The compensation element 18 with different delay segments shown in FIG. 9A. As long as the individual delay segments are shorted by the straight-line conductor segment, they effect no additional delay of the signal. Different line lengths and thus different delays can be generated via occurrence of individual corresponding segments of the straight-line conductor segments. For this purpose, the straight-line conductor segment is severed at the corresponding points in the production, for example chemically by etching, mechanically, by laser or ultrasonic ablation, or with other means. FIG. 9B shows the realization of an individual delay line ($\Delta t$). FIG. 9C shows the realization of three delay lines ($3 \times \Delta t$). FIG. 9D shows the realization of five delay lines ($5 \times \Delta t$), i.e., the maximum possibly delay with the shown compensation element. The length of the delay that is set in the respective compensation element 18 is selected dependent on the data rate (signal transmission time) to be transmitted with the transmission module. Naturally, such variable delays also can be realized other ways, for example by a different number of delay segments or different geometries of the compensation element. A strip conductor structure, however, is preferable on a printed circuit board that can be processed in a final etching step in order to adjust the desired delay (tuning). This delay is naturally precisely selected so that the unwanted time offset generated by the other components of the transmission module is at least approximately compensated so that the offset is minimized at the output of the connector 14.

A further measure for reduction of the common mode signal component on the strip conductor pair, namely an optimized termination 19 of the strip conductor pair, is also shown in FIG. 8. This optimized termination is also shown in an embodiment in FIGS. 3, 5 and 6. The common mode signal arising on the strip conductor pair 11 represents a significant factor when the line delay approaches a quarter of the signal period. In this case, small common mode artifacts from each signal edge build up and superimpose, period-by-period, to form increasing common mode signal noise at the receiver that leads to an amplification of the perturbing radiation. This problem is also known as common mode resonance. In order to avoid this common mode resonance, each strip conductor pair must have two terminations: a good differential termination at one or the other end in order to obtain a good differential signal quality, and a suitable common mode signal termination at one or the other end in order to prevent a common mode resonance. An ECL (Emitter Coupled Logic) driver as is frequently used in the transmission module does not effect a good common mode termination on the input side. In the device according to the present embodiment, a suitable common mode signal termination is therefore provided at the end of the strip conductor pair.

Figure 3:
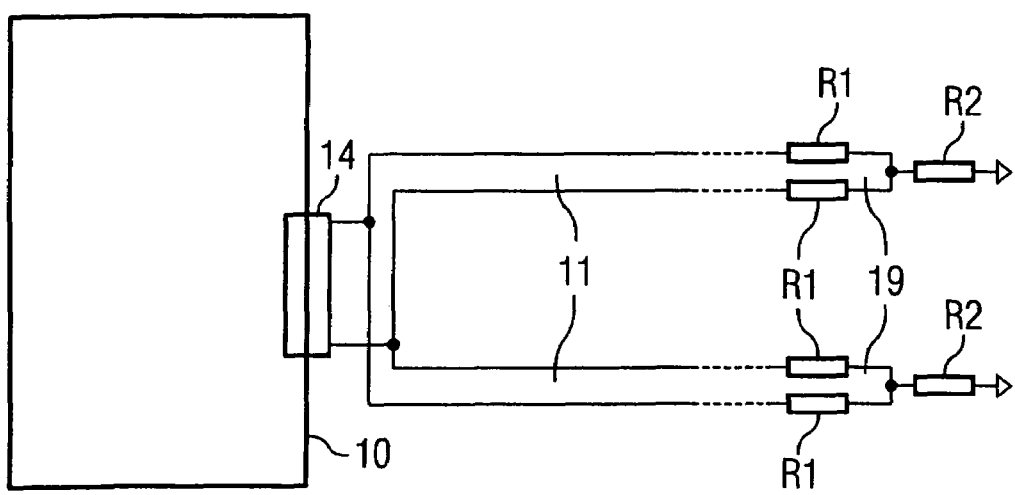
FIG. 3 is an example for the termination of the differential strip conductor pair according to the present invention.

In the present device, the strip conductors are thus suitably terminated not only for the differential signals but also for common mode signals. FIG. 3 shows an example for a suitable termination 19, in which a resistor termination network is formed from three resistors, two resistors $R_1$ and one resistor $R_2$. This T-shaped network composed of three resistors is selected such that $R_1+R_1=Z_D$ and $R_1/2+R_2=Z_{CM}$. $Z_D$ represents the differential resistance of the transmission line (i.e. of the strip conductor pair), $Z_{CM}$ represents the common mode resistance of the strip conductors of the strip conductor pair that are connected with one another.

Figure 4A:
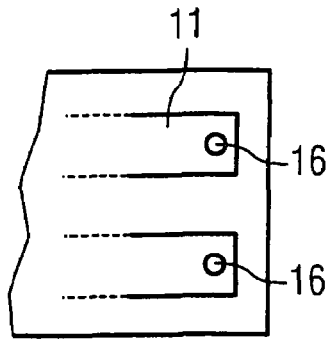
FIGS. 4A-4C show examples for the connection of the termination resistors with the strip conductor pair in accordance with the invention.
Figure 4B:
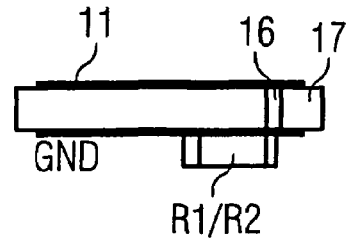
Figure 4C:
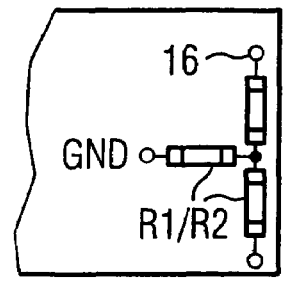

The resistors $R_1$, $R_2$ of the resistor network are preferably SMD resistors with optimally low tolerance and are attached to the underside of a printed circuit board 17 on which the strip conductors 11 run. The connection between the resistors R1, R2 and the strip conductor pair 11 also ensues here by feedthroughs 16 adapted in terms of impedance, such feedthroughs 16 already having been indicated in connection with FIG. 7. FIG. 4A shows a plan view, FIG. 4B shows a cross-section, and FIG. 4C shows a bottom view of a segment of the circuit board 17 with the corresponding strip conductors 11, feedthroughs 16 and resistors R1, R2.

FIGS. 10 through 13 show a further measure for minimization of the common mode signal component on the strip conductor pair, and thus for minimization of the electromagnetic perturbing radiation. Elements are hereby used that strongly suppress the common mode signal component on the strip conductor pair. FIG. 10 shows an example for a realization of these elements. In FIG. 10, the strip conductor pair 11 is divided into individual segments that are connected with one another by the elements 20 for common mode signal suppression, or which are at least partially enclosed by these elements 20.

An example for such elements 20 are common mode signal chokes 15 that connect the individual segments of the strip conductor pair 11 with one another. These common mode signal chokes 15 can be attached on the underside of a printed circuit board 17 on which the strip conductors 11 run. Here as well the electrical connection ensues by feedthroughs 16 adapted in terms of impedance, as is shown for the connection of two segments of the strip conductor pair 11 in FIG. 11A in plan view, FIG. 11B in cross-section, and FIG. 11C in the bottom view. The common mode signal chokes 15 are realized as SMD elements that strongly attenuate the common mode signal accumulated in the respective preceding segment.

A further possibility for realization of such elements 20 for common mode signal suppression is the use of ferrite rings that at least partially enclose the strip conductor pair. FIG. 12 shows an example for such an embodiment, in which a U-shaped element 21 made of ferrite material at least partially encloses the strip conductor pair. The strip conductor pair is attached at the rotating part 1 of a computed tomography apparatus. A strip 22 made of ferrite material is attached on the stationary part 2 in the immediate proximity of the strip conductor pair, the strip 22 at least approximately covers the channel formed by the U-shaped element 21. The individual U-shaped elements 21 behave as common mode chokes and thus improve the symmetry of the differential signal. The embodiment of FIG. 12 works particularly effectively against common mode currents that are induced in other passive metal parts in the immediate proximity of the strip conductor pair 11. Given use in a computed tomography apparatus these can be other slip rings in which energy is transmitted between the stationary part and the rotating part via carbon (graphite) brushes. Due to the prevention of injection (coupling) of common mode signal currents into these further slip rings, an uncontrolled, parasitic emission of perturbing radiation via this rings is prevented.

A further possibility for reduction or suppression of the common mode signal component on the strip conductor pair is the use of metallic structures in the form of capacitively-terminated and strongly-coupled stubs 23 on the printed circuit board. This is shown in FIGS. 13A and 13B, in which these stubs 23 are capacitively terminated by relatively large rectangular surfaces 24 on the printed circuit board. These stubs 23 act as chokes for the common mode signal. An efficient capacitive coupling to the reception element is additionally achieved by the termination of these stubs 23 with the relatively large surfaces 24. FIG. 13A shows a segment of the strip conductor pair 11 with the stubs 23 fashioned in-between. FIG. 13B shows an alternative circuit diagram of this embodiment.

The embodiments explained in connection with FIGS. 10 through 13B primarily serve for the suppression of a common mode signal component that would amplify during the signal transmission without these measures. Such common mode signal components already occur when the signal symmetry is disrupted (due to production inhomogeneities in the material of the circuit board for the strip conductors) since the signal propagates over relatively large distances of typically two to three meters along the strip conductor pair. This would lead to a continuously-growing common mode signal component, but this build up at all due to the measures described in the preceding. The electromagnetic perturbing radiation, that is generated by such common mode signal components thus is significantly reduced.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for non-contacting transmission of electrical signals between relatively movable parts, comprising:

a first part and a second part, one of said parts being movable relative to the other of said parts;

a transmission module on said first part that emits differential electrical signals;

a strip conductor pair on said first part and being supplied with said differential electrical signals omitted from said transmission module, said strip conductor pair comprising at least one component that reduces a common mode signal component in said strip conductor pair arising from said differential electrical signals in said strip conductor pair;

a reception element on said second part at a gap from said strip conductor pair being in a coupled relationship with said strip conductor pair during movement of said one of said parts to receive signals radiated by said strip conductor pair dependent on said differential electrical signals in said strip conductor pair; and a reception module in communication with said reception element supplied with said signals received by said reception element.

2. A device as claimed in claim 1 wherein said at least one component of said strip conductor pair comprises a plurality of resistors terminating said strip conductor pair for both said common mode signal component and a push-pull signal component.

3. A device as claimed in claim 2 wherein said termination resistors form a resistor T-network.

4. A device as claimed in claim 2 comprising a printed circuit board on which said strip conductor pair is attached at a first side, with said termination resistors being mounted on said printed circuit board at a second, opposite side, and said printed circuit board comprising feedthroughs electrically connecting said termination resistors with said strip conductor pair.

5. A device as claimed in claim 1 wherein said strip conductor pair comprises a plurality of segments, and wherein said at least one component comprises a plurality of common mode chokes respectively connected between said segments.

6. A device as claimed in claim 5 comprising a printed circuit board having a first side at which said segments of said strip conductor pair are disposed, and a second, opposite side at which said common mode chokes are mounted, said printed circuit board comprising a plurality of feedthroughs electrically connecting said common mode chokes with said segments of said strip conductor pair.

7. A device as claimed in claim 1 wherein said at least one component of said strip conductor pair is at least one element comprised of a ferrite material and at least partially enclosing said strip conductor pair.

8. A device as claimed in claim 7 comprising a plurality of elements of said ferrite material, distributed along a length of said strip conductor pair.

9. A device as claimed in claim 7 wherein said at least one element of said ferrite material comprises a single element extending continuously along a length of said strip conductor pair.

10. A device as claimed in claim 7 wherein said at least one element of said ferrite material comprises a first element forming a substantially U-shaped channel on said first part with said strip conductor pair being disposed in said channel, and a second element disposed on said second part overlying said strip conductor pair in said channel.

11. A device as claimed in claim 1 comprising a printed circuit board on which said strip conductor pair is disposed, said printed circuit board having a plurality of capacitively-terminated, closely-coupled stubs thereon electrically connected with said strip conductor pair and forming said at least one component.

12. A device as claimed in claim 11 comprising metallic surfaces on said circuit board that respectively capacitively terminate said stubs.

13. A device as claimed in claim I wherein said strip conductor pair has an input end into which said differential electrical signals are supplied, and wherein said at least one component comprises at least one common mode choke connected at said input end.

14. A device as claimed in claim 13 comprising a printed circuit board having a first side on which said strip conductor pair is disposed, and a second opposite side at which said common mode choke is mounted, said printed circuit board comprising a plurality of feedthroughs electrically connecting said common mode choke with said strip conductor pair.

15. A device for non-contacting transmission of electrical signals between two relatively movable parts, comprising:
a first part and a second part, one of said parts being movable relative to the other of said parts;
a transmission module at said first part that emits differential electrical signals at respective output conductors;
a strip conductor pair at said first part and connected to said output conductors of said transmission module and being supplied with said differential electrical signals therefrom, said strip conductor pair being susceptible to having a common mode signal component therein arising due to said differential electrical signals therein;
said transmission module comprising at least one compensation element connected to at least one of said output conductors that compensates a time offset between said differential electrical signals in the respective output conductors to reduce said common mode signal component in the differential electrical signals supplied to said strip conductor pair;
a reception element at said second part at a gap from said strip conductor pair and being in a coupled relationship with said strip conductor pair to receive signals radiated by said strip conductor pair dependent on said differential electrical signals therein; and
a reception module in communication with said reception element that is supplied with the signals received by said reception element.

16. A device as claimed in claim 15 wherein said compensation element is a delay element.

17. A device as claimed in claim 16 wherein said delay element is an adjustable delay element.

18. A computed tomography (CT) apparatus comprising:
a stationary part and a rotary frame rotatable within said stationary part;
an x-ray source and a radiation detector mounted on said rotary frame, said x-ray source emitting x-rays detected by said radiation detector while said rotary frame is rotating around an examination subject, to generate CT measurement data;
a transmission module at said rotary frame that emits differential electrical signals representing said CT measurement data;
a strip conductor pair at said first part and being supplied with said differential electrical signals emitted from said transmission module, said strip conductor pair comprising at least one component that reduces a common mode signal component in said strip conductor pair arising from said differential electrical signals in said strip conductor pair;
a reception element on said stationary part at a gap from said strip conductor pair and being in a coupled relationship with said strip conductor pair during rotation of said rotary frame to receive signals radiated by said strip conductor pair dependent on said differential electrical signals in said strip conductor pair; and
a reception module in communication with said reception element supplied with said signals received by said reception element.

19. A computed tomography (CT) apparatus for non-contacting transmission of electrical signals between two relatively movable parts, comprising:
a stationary part and a rotary frame rotatable within said stationary part;
an x-ray source and a radiation detector mounted on said rotary frame, said x-ray source emitting x-rays detected by said radiation detector while said rotary frame is rotating around an examination subject, to generate CT measurement data;
a transmission module that emits differential electrical signals at respective output conductors representing said CT measurement data;
a strip conductor pair at said first part and connected to said output conductors of said transmission module and being supplied with said differential electrical signals therefrom, said strip conductor pair being susceptible to having a common mode signal component therein arising due to said differential electrical signals;
said transmission module comprising at least one compensation element connected to at least one of said output conductors that compensates a time offset between said differential electrical signals in the respective output conductors to reduce said common mode signal component in the differential signals supplied to said strip conductor pair;

a reception element at said stationary part and at a gap from said strip conductor pair and being in a coupled relationship with said strip conductor pair during rotation of said rotary frame to receive signals radiated by said strip conductor pair dependent on said differential electrical signals therein; and a reception module in communication with said reception element that is supplied with the signals received by said reception element.

* * * * *